United States Patent [19]

Arp

[11] 4,401,431
[45] Aug. 30, 1983

[54] BLOOD PUMP AND OXYGENATOR MONITOR-CONTROLLER AND DISPLAY DEVICE

[76] Inventor: Leon J. Arp, 1107 Highland Cir., S.E., Blacksburg, Va. 24060

[21] Appl. No.: 277,887

[22] Filed: Jun. 26, 1981

[51] Int. Cl.³ .............................................. A61M 1/03
[52] U.S. Cl. .................................. 604/4; 128/DIG. 3; 422/44; 422/45; 604/5; 604/6; 604/31; 604/50
[58] Field of Search ............ 128/214 E, 214 F, 24 R, 128/1 D, 214 R, 762, 700, 96, 670, 671, 672, DIG. 3; 422/44–45; 604/4–6, 31, 50, 65–67

[56] References Cited

U.S. PATENT DOCUMENTS

| 3,946,731 | 3/1976 | Lichtenstein | 128/214 R |
| 3,985,123 | 10/1976 | Herzlinger | 128/1 D |
| 4,148,314 | 4/1979 | Yin | 128/214 E |
| 4,321,929 | 3/1982 | Lamelson et al. | 128/700 |
| 4,326,513 | 4/1982 | Schulz et al. | 128/671 |

*Primary Examiner*—Richard J. Apley
*Assistant Examiner*—George Yanulis
*Attorney, Agent, or Firm*—Henderson & Sturm

[57] ABSTRACT

A blood pump and oxygenator monitor-controller and display device is disclosed. The device includes a plurality of data communication ports, a plurality of data and output control ports all operably connected to decision making or computer circuitry, and a plurality of digital and/or analog displays or controlling means responsive thereto for the purposes of displaying measured and calculated data and/or for monitoring and controlling the operation of various sub-systems contained in a blood pumping and oxygenating system.

20 Claims, 1 Drawing Figure

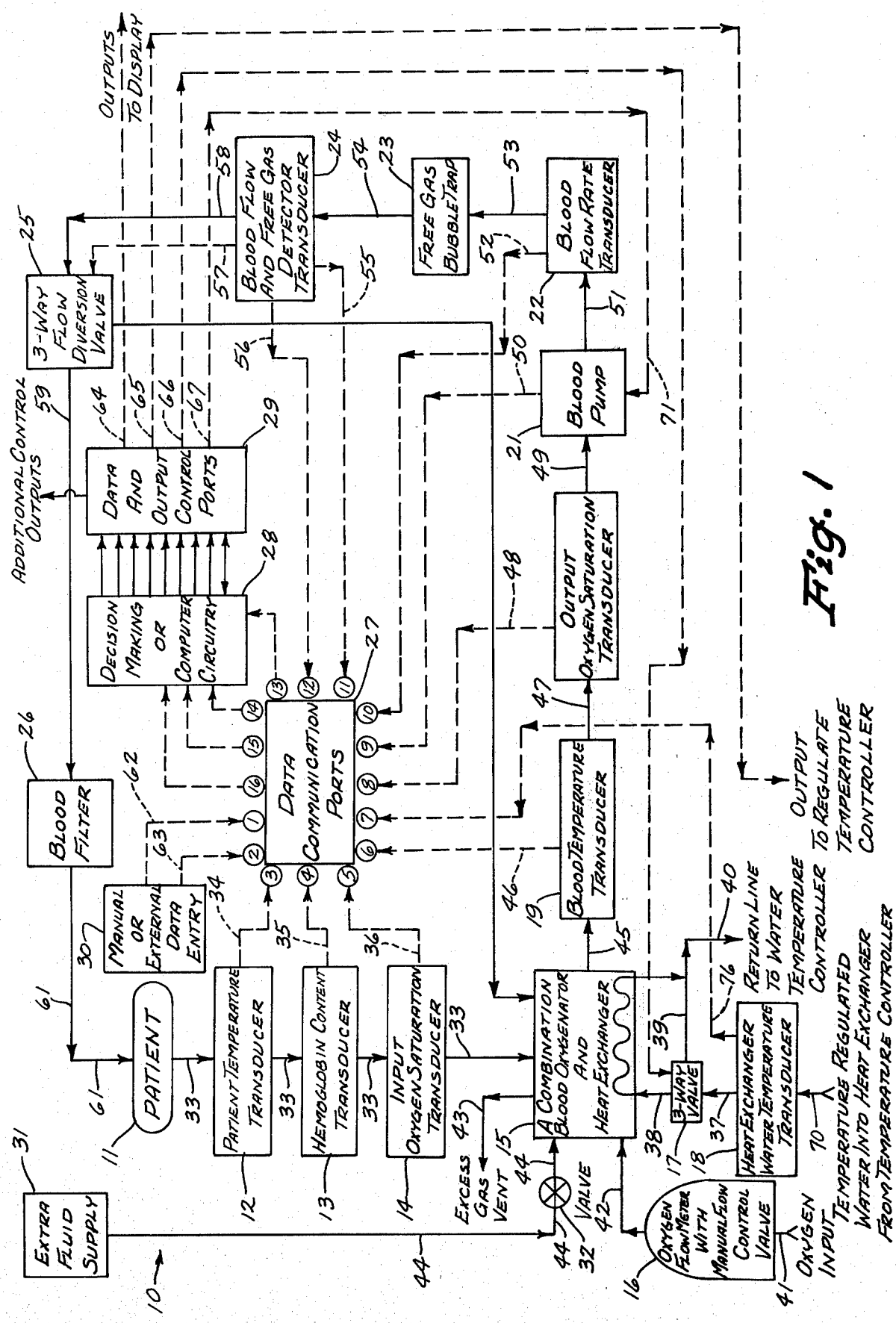

BLOOD PUMP AND OXYGENATOR MONITOR-CONTROLLER AND DISPLAY DEVICE

BACKGROUND OF THE INVENTION

This invention relates generally to the art of extracorporeal blood pumping and oxygenation, and more particularly to the art of acquiring, processing, and displaying data for the purposes of providing information to the attending medical personnel of the condition of a patient and the operating characteristics of the blood pumping and oxygenating devices while at the same time automatically using the acquired and calculated data to accurately control the operation of the various sub-systems which make-up the entire extracorporeal blood pumping and oxygenating system.

At present such extracorporeal blood pumping and oxygenating systems are used almost exclusively in open heart surgical procedures where the normal blood flow through the heart and lungs of the patient is interrupted or bypassed. Even a relatively simple system contains several other devices in addition to the basic blood pump and oxygenator. It is essential for the well being of the patient that every device in the system functions perfectly and that any malfunction be detected and corrected as soon as possible. At present the operation of the devices in the system is monitored visually and controlled by the attending personnel. It is not now possible to continuously monitor, display, and use this data to automatically control the devices in the system. The invention makes it possible to continuously monitor, display and to use the acquired and calculated data to automatically optimize the control and operation of the extracorporeal blood pumping and oxygenating system.

At present there is no method or device available for the medical personnel to use to continuously determine the metabolic oxygen consumption of a patient undergoing a total cardio-pulmonary bypass procedure using an extracorporeal blood pumping and oxygenating system. Continuous knowledge of this physiologic parameter would be of great potential value to both the patient and the attending medical personnel. With the use of this invention, it becomes possible, for the first time, to continuously determine and display the metabolic oxygen consumption of a patient undergoing a total cardiopulmonary bypass procedure.

SUMMARY OF THE INVENTION

It is, therefore, a primary object of this invention to provide a blood pump and oxygenator monitor-controller and display device.

It is another object of this invention to provide a blood pump and oxygenator monitor-controller and display device that will accept a plurality of input signals from devices used to monitor the medical conditions of a patient and/or the operating parameters of various devices in an extracorporeal blood pumping and oxygenating system.

It is another object of this invention to provide a blood pump and oxygenator monitor-controller that will display a plurality of measured and calculated input data.

It is another object of this invention to provide a blood pump and oxygenator monitor-controller and display device that utilizes a digital and/or analog computer to control the display of measured data and to use the measured data to calculate and then display additional data useful to the attending medical personnel.

It is another object of this invention to provide a blood pump and oxygenator monitor-controller and display device that will utilize the decision making capabilities of either dedicated circuitry and/or a computer to control and alter the operating characteristics of a plurality of devices attached to the controlling output ports of the computer.

It is yet another object of this invention to provide a blood pump and oxygenator monitor-controller that is economical to manufacture, durable of construction, efficient in use, and is accurate and precise in displaying measured data and controlling the operating parameters of various devices in the extracorporeal blood pumping and oxygenating system.

These objects and others are realized by the provision of a blood pump and oxygenator monitor-controller and display device. The blood pump and oxygenator monitor-controller and display device includes a plurality of input data communication ports and data and output control ports operably connected to decision making or computer circuitry for the purpose of interfacing input data transducers with the decision making or computer circuitry and for interfacing the decision making or computer circuitry through the data and output control ports to the data display units and the sub-systems to be controlled by the blood pump and oxygenator monitor-controller and display device, a plurality of digital and/or analog displays or controlling means responsive thereto for displaying measured and calculated data and/or for controlling the operation of various sub-systems of a blood pumping and oxygenating system.

BRIEF DESCRIPTION OF THE DRAWING

These objects will become more readily apparent upon reference to the following detailed description, and especially when studied in conjunction with the appended drawings, wherein:

FIG. 1 is a block diagram of the preferred embodiment of the invention as applied to a generalized configuration of a blood pumping and oxygenating system.

DESCRIPTION OF THE PREFERRED EMBODIMENT

With reference to FIG. 1, the preferred embodiment of a generalized blood pumping and oxygenating system similar to those currently used widely in medical practice may be seen as denoted generally by the numeral 10. More specifically, the preferred embodiment 10 includes the patient 11, a patient temperature transducer 12, a hemoglobin content transducer 13, an input oxygen saturation transducer 14, a combination blood oxygenator and heat exchanger 15, an oxygen flow meter with manual flow control valve 16, a 3-way valve 17, a heat exchanger water temperature transducer 18, a blood temperature transducer 19, an output oxygen saturation transducer 20, a blood pump 21, a blood flow rate transducer 22, a free gas bubble trap 23, a blood flow and free gas detector transducer 24, a 3-way flow diversion valve 25, a blood filter 26, a plurality of data communication ports 27, decision making or computer circuitry 28, a plurality of data and output control ports 29, a plurality of manual or external data entry ports 30, an extra fluid supply 31, a valve 32, the fluid transmission conduit or tubing denoted by solid lines connecting the sub-systems, and the monitoring, display, and controlling signal lines for the sub-systems denoted by dashed or broken lines. For the purpose of this disclosure, the preferred embodiment 10 of the apparatus and the operation thereof will be disclosed for accomplishing the teachings of the preferred embodiment 10.

The embodiment 10 as represented herein is for the realization of a generalized blood pumping and oxygenating system. It will be well understood by those skilled in the art that the principles taught herein may easily be contracted or expanded to produce a blood pump and oxygenator monitor-controller and display device able to monitor, display, and control fewer or more operating parameters and/or sub-systems.

Many of the sub-systems illustrated in the embodiment 10 are commercially available and widely used, therefore, the subject of the following description of the present invention is that of a blood pump and oxygenator monitor-controller and display device only.

For the purpose of describing the operation of the invention refer to embodiment 10 where the flow of blood from the patient through the various sub-systems and then back to the patient will be described. The purpose or operation of each sub-system will be described in sequence as the blood flow is traced from one sub-system to another thereby providing a complete understanding of the operation of the invention.

Blood requiring removal of carbon dioxide and the addition of oxygen flows through a hollow conduit or tube 33 and through the patient temperature transducer 12. The temperature transducer 12 may be of any suitable conventional type. The patient temperature transducer 12 produces an output signal proportional to the temperature of the patient's blood. This signal is then transmitted over the signal line 34 to input 3 of the data communication port 27. The blood then flows through the hemoglobin content transducer 13 which produces an output signal proportional to the total amount of hemoglobin in the blood. This signal is then routed over the signal line 35 to input 4 of the data communication port 27. Next, the blood flows through the input oxygen saturation transducer 14 which produces an output signal proportional to the percent of the total hemoglobin content which is saturated with oxygen. This signal is then routed over the signal line 36 to input 5 of the data communication port 27. The blood then flows through the combination blood oxygenator and heat exchanger 15 where it is oxygenated, has carbon dioxide removed, and is heated or cooled by contact with the heat exchanger unit. The heat exchanger may be built into the blood oxygenator 15 or may be a separate unit preceeding or following the blood oxygenator. Temperature regulated water from an external source enters the system through fluid conduit 70 and flows through the heat exchanger water temperature transducer 18 which produces an output signal proportional to the temperature of the water entering the system. This signal is then transmitted over the signal line 76 to input 7 of the data communication port 27. The water then flows through fluid conduit 37 and 3-way valve 17. The 3-way valve 17 is used to direct the flow of water either through the fluid heat exchanger conduit 38 and through the heat exchanger in the combination blood oxygenator and heat exchanger 15 or causes the water to be shunted or directed away from the combination blood oxygenator and heat exchanger 15 and through fluid conduit 39 which is operably connected to the return line 40 of the external water temperature controller. Oxygen enters the oxygen flow meter with manual flow control valve 16 through fluid conduit 41 and is delivered through fluid conduit 42 to the combination blood oxygenator and heat exchanger 15. Any excess gas delivered to the combination blood oxygenator and heat exchanger 15 is vented to the atmosphere through fluid conduit 43. In the event that extra fluid, which may or may not be blood, is needed for the patient, the valve 32, which is interposed in the fluid conduit 44 connecting the extra fluid supply 31 to the combination blood oxygenator and heat exchanger 15, may be opened to allow the extra fluid supply 31 to flow through fluid conduit 44, and valve 32 into the combination blood oxygenator and heat exchanger 15. Blood and/or fluid leaves the combination blood oxygenator and heat exchanger 15 through fluid conduit 45 and flows through the blood temperature transducer 19 which produces an output signal proportional to the temperature of the blood leaving the combination blood oxygenator and heat exchanger 15. This signal is then transmitted over the signal line 46 to input 6 of the data communication port 27. Blood next flows through fluid conduit 47 into the output oxygen saturation transducer 20 which produces an output signal proportional to the percent of the total hemoglobin content which is saturated with oxygen. This signal is then routed over the signal line 48 to input 8 of the data communication port 27. Blood leaves the output oxygen saturation transducer through fluid conduit 49 and flows into the blood pump 21. A signal representing the operating status of the blood pump 21 is transmitted over signal line 50 to input 9 of the data communication port 27. Operation of the blood pump 21 can be altered by control signals transmitted on the control line 71 which operably connected the blood pump 21 to one of the data and output control ports 29. Blood is pumped through fluid conduit 51 into the blood flow rate transducer 22 which produces a signal proportional to the blood flow rate through the extracorporeal circuit. This is then routed over signal line 52 to input 10 of the data communication port 27. The blood next flows through the fluid conduit 53 to the free gas bubble trap 23 where it is intended that all free gas bubbles which may be entrained in the flowing blood will be trapped and removed from the blood before the flow leaves the free gas bubble trap 23 through fluid conduit 54. The blood flow enters the blood flow and free gas detector transducer 24 which contains two sensing units. The first sensor determines whether the blood is sensed to be flowing or not flowing. If no blood flow is sensed, the blood flow and free gas detector transducer 24 produces a warning signal which is transmitted over the signal line 55 and is delivered to input 11 of the data communication port 27. The warning signal indicates to the system and medical personnel that the second sensing unit in the blood flow and free gas detection transducer 24 most likely would not be able to sense the presence of free gas in the blood flowing through it. If, however, free gas is detected in the blood flowing past the second sensor to the 3-way flow diversion valve 25 through fluid conduit 58, an alarm signal is delivered over signal line 56 to input 12 of the data communication port 27. At the same time, a control signal is delivered over control line 57 to the 3-way flow diversion valve 25 which causes the valve to immediately stop the flow of blood to the patient through fluid conduit 59 and redirects or diverts the blood flow through fluid conduit 60 and back to the output side of the combination blood oxygenator and heat exchanger 15 thereby preventing a life threatening gas embolism. When no more free gas is detected in the blood by the second sensor in the blood flow and free gas detector transducer 24 an appropriate signal is delivered over the signal line 56 to input 12 of the data communication port 27 thereby cancelling the previous alarm condition. At the same time, the control signal on the control line 57 which originated from the blood flow and free gas detector transducer is removed thereby causing the 3-way flow diversion valve 25 to stop the blood flow through fluid conduit 60 and to re-establish the blood flow to the patient through fluid conduit 59. Oxygenated blood is finally returned to the patient through the blood filter 26 and the fluid conduit 61.

Signals from the patient temperature transducer 12, hemoglobin content transducer 13, input oxygen saturation transducer 14, heat exchanger water temperature transducer 18, blood temperature transducer 19, output oxygen saturation transducer 20, blood pump 21, blood flow rate transducer 22, and the blood flow and free gas detector transducer 24 are all routed into the data communication ports 27. In addition, manual or external data entry unit 30 allows the operator to enter data and/or operating parameters through inputs 1 and 2 of the data communication port 27 over signal lines 62 and 63 respectively. The inputs directed through the data communication ports 27 are routed to the decision making or computer circuitry 28 where appropriate display and control signals are generated and delivered to the data and output control ports 29. The data and output control ports 29 provide the appropriate interfacing circuitry to implement the display and control functions desired.

The type of signal, analog and/or digital, provided by the data and output control ports 29 will depend upon what element or device is to be driven or caused to operate. To illustrate this point, examples will now be given of the types of signals which would be generated by the data and output control ports 29 and carried by output control lines 64, 65, 66 and 67 to each element or device being driven or caused to operate. It should be noted that the input data lines 34, 35, 36, 46, 76, 48, 50, 52, 55, and 56 as well as the output control lines 64, 65, 66, and 67 are depicted in schematic form in the preferred embodiment 10, and therefore, each of these input and output lines may be made up of a plurality of signal carrying lines. Consequently, the output control line 64 could drive a plurality of either digital and/or analog type display units. For illustration of the preferred embodiment 10, the output control line 64 would drive display units indicating the temperature of the patient as measured by the patient temperature transducer 12, the total hemoglobin content of the blood as measured by the hemoglobin content transducer 13, the percent of the total hemoglobin saturated with oxygen as measured by the input oxygen saturation transducer 14, the temperature of the water flowing into the heat exchanger as measured by the heat exchanger water temperature transducer 18, the temperature of the blood leaving the combination blood oxygenator and heat exchanger 15 as measured by the blood temperature transducer 19, the percent of the total hemoglobin content of the blood saturated with oxygen after the blood has been oxygenated as measured by the output oxygen saturation transducer 20, the volume flow of blood per unit of time as measured by the blood flow rate transducer 22, and the output status of the blood flow and free gas detector transducer 24 indicating whether or not blood flow was being detected and whether or not free gas in the flowing blood was detected. In addition to displaying the various detected and measured parameters, the blood pump and oxygenator monitor-controller and display device would also be able to derive and display such operating parameters as speed of the blood pump 21, and therefore, blood flow rate for comparison to the measured blood flow rate as detected by the blood flow rate transducer 22. Such comparisons would be made by the decision making or computer circuitry 28. This circuitry, when provided with all of the input data described previously, can calculate and display many other useful relationships such as the difference between the percent of the total hemoglobin in the blood which is saturated with oxygen from the blood entering and leaving the combination blood oxygenator and heat exchanger 15.

The stoichiometric oxygen capacity of hemoglobin may be computed from its molecular weight and the molar volume of oxygen. As one mole of oxygen at STP is equivalent to 22,414 milliliters and as human hemoglobin has a typical molecular weight of 64,458 grams per mole and an equivalent weight one-fourth this, one gram of hemoglobin can combine with 1.39 milliliters of oxygen (from the Annual Meeting International Committee for Standardization in Hematology, 1966). Therefore, by entering this data into the decision making or computer circuitry 28 by way of a program element in the computer or from the manual or external data entry unit 30 which is operably connected to the decision making or computer circuitry 28 through the data communication ports 27, the oxygen content of the blood may be determined or calculated and this displayed from the data and output control ports 29 by using the following mathematical relationship:

$$\text{Oxygen content} = 1.39 \times \text{Hemoglobin} \times \frac{\% \text{ Hemoglobin Saturated with oxygen}}{100}$$

where hemoglobin and the percent hemoglobin saturated with oxygen are expressed to a common base. That is, both the hemoglobin concentration and the percent of the hemoglobin saturated with oxygen must relate either to the total amount of hemoglobin or to the hemoglobin available for oxygenation. Both approaches are equivalent.

At present there is no method or device available for the medical presonnel to use to be able to continuously determine the metobolic oxygen consumption of a patient undergoing a total cardio-pulmonary bypass procedure using an extracorporeal blood pumping and oxygenating system. Continuous knowledge of this physiologic parameter would be of great potential value to both the patient and the attending medical personnel. When all of the input data described previously is available, it becomes possible, for the first time, to continuously determine and display the metabolic oxygen consumption of a patient undergoing a total cardio-pulmonary bypass procedure. The mathematical relationship required to make this calculation is:

oxygen consumption per minute equals:

blood hemoglobin content × blood flow rate ×
    oxygen binding capacity of blood ×
(output oxygen saturation of blood − input saturation of blood) =

$$\frac{\text{grams Hemoglobin}}{100 \text{ milliliters}} \times \frac{\text{milliliters}}{\text{minute}} \times \frac{1.39 \text{ milliliters}}{\text{gram hemoglobin}} \times$$

change in % hemoglobin saturated with oxygen =
milliliters of oxygen consumed per minute.

It should be obvious from the above to anyone skilled in the art that the number of operating parameters which can be monitored, determined, or calculated and displayed by the system is limited only by the form and the number of data inputs supplied to the system's data communication ports 27.

Other illustrations of the preferred embodiment 10 follow. The output control line 65 would deliver an analog and/or digital control signal to the input of the external water temperature controller. Output control line 66 would deliver a control signal to the 3-way valve 17 which would either allow the temperature regulated water from the external temperature controller to flow through the heat exchanger contained in the combination blood exygenator and heat exchanger 15, or to direct the flow of water through fluid conduits 39 and 40 to return the water to the external temperature controller without passing through the heat exchanger. The output control line 67 would deliver an analog and/or digital control signal to the controlling sub-system of the blood pump 21 for the purpose of controlling the blood flow rate through the extracorporeal blood circuit.

It is obvious from the above to anyone skilled in the art that the number of operating parameters which can be controlled by the data and output control ports 29 is limited only by the number of data inputs provided in the system's data communication ports 27 and/or by the number of data and output control ports 29 which are provided.

The types of data communication ports 27 and data and output control ports 29 which would be used to construct the blood pump and oxygenator monitor-controller and display device will be mandated by the type of decision making or computer circuitry 28 which is used. Such decisions and their implementation would be accomplished easily by all who are ordinarily skilled in the art.

Many variations of the embodiment disclosed here will be obvious to those skilled in the art. Some examples of such variations could include the use of only analog type circuitry, the use of only digital type circuitry, the use of a combination of analog and digital circuitry, and the use of hydraulic or other type signals separately or in combination with those listed previously. It is to be understood that these and other variations are not to be taken as outside the intent and scope of the appended claims.

I claim:

1. A blood pump and oxygenator monitor-controller and display device comprising:
    a plurality of sub-systems, said sub-systems being connected in fluid communication by a plurality of conduits, said conduits being connected to the blood supply of a patient, said blood supply being circulated from said patient through said subsystems and conduits and then back to said patient, said subsystems including transducers means for sensing parameter values of said blood supply and converting said parameter values into data input signals;
    a plurality of data communication ports for receiving data input signals from said transducer means and being operably connected to decision making circuitry, said data communication ports transmitting said data input signals from said transducer means to said decision making circuitry;
    a plurality of data output ports operably connected to said decision making circuitry for the purpose of receiving a plurality of signals produced by said decision making circuitry;
    a plurality of data display devices operably connected to said data output ports for the purpose of receiving and displaying a plurality of signals transmitted from said data output ports;
    a plurality of output control ports operably connected to said decision making circuitry for the purpose of receiving a plurality of signals produced by said decision making circuitry, said output control ports being operably connected to one or more of said sub-systems to modify the response or operation of the said sub-systems.

2. A blood pump and oxygenator monitor-controller and display device comprising:
    a plurality of sub-systems, said sub-systems being connected in fluid communication by a plurality of conduits, said conduits being connected to the blood supply of a patient, said blood supply being circulated from said patient through said sub-systems and conduits and then back to said patient, said sub-systems including transducer means for sensing parameter values of said blood supply and converting said parameter values into data input signals;
    a plurality of data communication ports for receiving data input signals from said transducer means, and containing multiplexing circuitry for the purpose of sequentially inputing signals from said transducer means to analog-to-digital converter circuitry, said data communication ports being operably connected to a digital computer for the purpose of transmitting input data to the said digital computer;
    a plurality of digital type data output ports operably connected to said digital computer for the purpose of receiving a plurality of signals produced by said digital computer;
    a plurality of digital type data display devices operably connected to said data output ports for the purpose of receiving and displaying a plurality of signals transmitted from said data output ports;
    a plurality of digital type output control ports operably connected to said digital computer for the purpose of receiving a plurality of signals produced by said digital computer, said output control ports also being operably connected to said sub-systems to modify the response or operation of said sub-systems.

3. A blood pump and oxygenator monitor-controller and display device as defined in claim 2, wherein a plurality of said digital type data output ports contain digital-to-analog converters for the purpose of receiving a plurality of digital signals from the said digital computer and for converting said digital signals to a plurality of analog type display signals.

4. A blood pump and oxygenator monitor-controller and display device as defined in claim 3, wherein a plurality of linear type data display devices are operably connected to said data output ports, said linear type display devices receiving and displaying a plurality of analog signals transmitted from said data output ports, and wherein a plurality of said digital type control ports contain digital-to-analog converters for the purpose of receiving a plurality of digital signals from said digital computer and for converting said digital signals to a plurality of analog type control signals, said analog type control signals being transmitted to said sub-systems to modify the response or operation thereof.

5. A blood pump and oxygenator monitor-controller and display device comprising:

a plurality of sub-systems, said sub-systems being connected in fluid communication by a plurality of conduits, said conduits being connected to the blood supply of a patient, said blood supply being circulated from said patient through said sub-systems and conduits and then back to said patient, said sub-systems including transducer means for sensing parameter values of said blood supply and converting said parameter values into data input signals;

a plurality of data communication ports for receiving data input signals from said transducer means and containing analog type circuitry for the purpose of receiving and conditioning analog type signals supplied to the inputs of said data communication ports by said transducer means, said data communication ports being operably connected to an analog type computer, said analog computer making comparisons between and among said input signals, performing calculations and producing a plurality of analog type output signals;

a plurality of analog type data output ports operably connected to said analog computer for the purpose of receiving a plurality of signals produced by said computer;

a plurality of analog type data display devices operably connected to said data output ports for the purpose of receiving and displaying a plurality of signals transmitted from said data output ports;

a plurality of analog type output control ports operably connected to said analog computer for the purpose of receiving a plurality of signals produced by said analog computer said output control ports being operably connected to said sub-systems to produce a plurality of control signals which modify the response or operation of said sub-systems.

6. A blood pump and oxygenator monitor-controller and display device as defined in claim 5, wherein a plurality of said analog type data output ports contain analog-to-digital converters for the purpose of receiving a plurality of analog signals from the said analog computer and for converting said analog signals to a plurality of digital type display signals.

7. A blood pump and oxygenator monitor-controller and display device as defined in claim 6, wherein a plurality of digital type data display devices are operably connected to said data output ports for receiving and displaying a plurality of digital signals transmitted from said data output ports, and wherein a plurality of linear type control ports operably connected to said digital computer contain analog-to-digital converters for the purpose of receiving a plurality of analog signals from said analog computer and for converting said analog signals to a plurality of digital type control signals said digital type control signals modifying the response or operation of said sub-systems.

8. A blood pump and oxygenator monitor-controller and display device comprising:

a plurality of sub-systems, said sub-systems being connected in fluid communication by a plurality of conduits, said conduits being connected to the blood supply of a patient, said blood supply being circulated from said patient through said sub-systems and conduits and then back to said patient, said sub-systems including transducer means for sensing parameter values of said blood supply and converting said parameter values into data input signals;

a plurality of data communication ports for receiving data input signals from said transducer means and being operably connected to decision making circuitry for the purpose of receiving a plurality of data input signals and transmitting said data input signals to said decision making circuitry, said data input signals including data for total hemoglobin content, blood flow rate, the percent of the total hemoglobin content which is saturated with oxygen for the blood entering a blood oxygenator sub-system, the percent of the total hemoglobin content which is saturated with oxygen for the blood leaving said blood oxygenator sub-system, the temperature of the blood leaving said blood oxygenator sub-system and the heat exchanger water temperature, said decision making circuitry using said data to calculate the amount of oxygen transferred per minute by said blood oxygenator sub-system to the blood flowing through said device;

a plurality of data output ports operably connected to said decision making circuitry for the purpose of receiving a plurality of signals produced by said decision making circuitry;

a plurality of data display devices operably connected to said data output ports for the purpose of receiving and displaying a plurality of signals transmitted from said data output ports;

a plurality of output control ports operably connected to said decision making circuitry for the purpose of receiving a plurality of signals produced by said decision making circuitry, said output control ports being operably connected to one or more of said sub-systems and producing a plurality of control signals to modify the response or operation of the said sub-systems.

9. A blood pump and oxygenator monitor-controller and display device as defined in claim 2, wherein said input signals from said transducers means include data for total hemoglobin content of the blood flowing through the device, blood flow rate, the percent of the total hemoglobin content which is saturated with oxygen for the blood entering a blood oxygenator sub-system, the percent of the total hemoglobin content which is saturated with oxygen for the blood leaving said blood oxygenator, the temperature of the blood leaving said blood oxygenator, and the heat exchanger water temperature; and wherein the said digital computer uses said data to calculate the amount of oxygen transferred per minute by the blood oxygenator to the blood flowing through the device, said calculation being transmitted to and displayed by said display device.

10. A blood pump and oxygenator monitor-controller and display device as defined in claim 9, wherein a plurality of said digital type data output ports contain digital-to-analog converters for the purpose of receiving a plurality of digital signals from the said digital computer and for converting said digital signals to a plurality of analog type display signals.

11. A blood pump and oxygenator monitor-controller and display device as defined in claim 10, wherein a plurality of linear type data display devices are operably connected to said data output ports for the purpose of receiving and displaying a plurality of analog signals transmitted from said data output ports, and wherein a plurality of said digital type control ports contain digital-to-analog converter for the purpose of receiving a plurality of digital signals from said digital computer and for converting said digital signals to a plurality of analog type control signals, said analog type control signals modifying the response or operation of said sub-systems.

12. A blood pump and oxygenator monitor-controller and display device as defined in claim 5, wherein the said analog type signals supplied to the inputs of said data communication ports include data for total hemoglobin content of the blood flowing through the device, blood flow rate, the percent of the total hemoglobin content which is saturated with oxygen for the blood entering a blood oxygenator sub-system, the percent of the total hemoglobin content which is saturated with oxygen for the blood leaving said blood oxygenator sub-system, the temperature of the blood leaving said blood oxygenator sub-system, and the water temperature of a heat exchanger sub-system.

13. A blood pump and oxygenator monitor-controller and display device as defined in claim 12, wherein a plurality of analog type data output ports contain analog-to-digital converters for the purpose of receiving a plurality of analog signals from the said analog computer and for converting said analog signals to a plurality of digital type signals.

14. A blood pump and oxygenator monitor-controller and display device as defined in claim 13, wherein a plurality of digital type data display devices are operably connected to said data output ports for the purpose of receiving and displaying a plurality of digital signals transmitted from said data output ports, and wherein a plurality of linear type control ports operably connected to said analog computers contain analog-to-digital converters for the purpose of receiving a plurality of analog signals from said analog computer and for converting said analog signals to a plurality of digital type control signals, said digital type control signals modifying the response or operation of one or more of said sub-systems.

15. A blood pump and oxygenator monitor-controller and display device comprising:
 a plurality of sub-systems, said sub-systems being connected in fluid communication by a plurality of conduits, said conduits being connected to the blood supply of a patient, said blood supply being circulated from said patient through said sub-systems and conduits and then back to said patient, said sub-systems including transducer means for sensing parameter values of said blood supply and converting said parameter values into data input signals;
 a plurality of data communication ports receiving data input signals from said transducer means and containing multiplexing circuitry for the purpose of inputing signals from said transducer means to analog-to-digital converter circuitry and operably connected to a digital computer, said digital computer performing calculations and making logical decisions, said input signals from said transducer means including data for total hemoglobin content of the blood flowing through the device, blood flow rate, the percent of the total hemoglobin content which is saturated with oxygen for the blood entering a blood oxygenator sub-system, the percent of the total hemoglobin content which is saturated with oxygen for the blood leaving said blood oxygenator, the temperature of the blood leaving said blood oxygenator, and the water temperature of a heat exchanger sub-system; and wherein said digital computer performs calculations to determine the amount of oxygen transferred per minute by said blood oxygenator sub-system to the blood flowing through the device;
 a plurality of digital type data output ports operably connected to said digital computer for the purpose of receiving plurality of signals produced by said digital computer;
 a plurality of digital type data display devices operably connected to said data output ports for the purpose of receiving and displaying a plurality of signals transmitted from said data output ports;
 a plurality of digital type output control ports operably connected to said digital computer for the purpose of receiving plurality of signals produced by said digital computer, said output control ports also operably connected to one or more of said sub-systems to produce a plurality of control signals to modify the response of said sub-systems.

16. A blood pump and oxygenator device, said device being connected to a patient for extracorporeal blood pumping and oxygenation of the patient's blood supply during surgical procedures, comprising:
 a plurality of sub-systems including a blood oxygenator and blood pump;
 conduit means for fluidly connecting said sub-systems to the blood supply of the patient so that the blood supply circulates through said sub-systems;
 said sub-systems further including transducer means in fluid communications with the blood supply flowing through said blood oxygenator and said blood pump, said transducer means sensing values of parameters of the blood supply and converting said parameter values into electrical signals;
 at least one signal line in electrical connection with said transducer means; and
 a means for displaying one or more of said parameter values, said parameter values being transmitted from said transducer means over said signal line to said display means.

17. The blood pump and oxygenator device of claim 16 wherein said signal lines are operably connected between said transducer means and a plurality of data communication ports, said data communication ports being operably connected to decision making and computing circuitry, said decision making and computing circuitry having at least one output operably connect to said display means.

18. The blood pump and oxygenator device of claim 16, further comprising a means for controlling one or more of said sub-systems in response to parameter values sensed by said transducer means.

19. The blood pump and oxygenator device of claim 16. wherein said transducer means includes a hemoglobin content transducer, an input oxygen saturation transducer operationally preceeding said blood oxygenator, an output oxygen saturation transducer operationally subsequent said blood oxygenator, and a blood flow rate transducer, the electrical output of said transducers being electrically input to computer circuitry wherein the metabolic oxygen consumption of the patient is calculated, said computer circuitry having an output operatively connected to said displaying means, said metabolic oxygen consumption being displayed by said displaying means.

20. The blood pump and oxygenator device of claim 17, wherein said transducer means further comprises a free gas detector transducer, said free gas detector transducer being operatively connected to a means for controlling a diversion valve, said free gas detector activating said diversion valve to divert the blood flowing through the device from flowing to the patient whenever free gas is detected in the blood flowing through the device by said free gas detector transducer.

* * * * *